United States Patent [19]

Fabinski et al.

[11] 4,281,248
[45] Jul. 28, 1981

[54] NONDISPERSIVE INFRARED GAS ANALYZER

[75] Inventors: Walter Fabinski, Kriftel; Udo Deptolla, Ober-Olm, both of Fed. Rep. of Germany

[73] Assignee: Hartmann & Braun Aktiengesellschaft, Frankfurt am Main, Fed. Rep. of Germany

[21] Appl. No.: 145,364

[22] Filed: Apr. 30, 1980

[30] Foreign Application Priority Data

May 5, 1979 [DE] Fed. Rep. of Germany ....... 2918207

[51] Int. Cl.$^3$ ............................................. G01N 21/26
[52] U.S. Cl. ..................................... 250/345; 250/343
[58] Field of Search .................... 250/343, 345, 346; 356/51, 306, 437

[56] References Cited

U.S. PATENT DOCUMENTS

| | | | |
|---|---|---|---|
| 3,925,667 | 12/1975 | Staab | 250/344 |
| 3,937,962 | 2/1976 | Faulhaber et al. | 250/346 |
| 3,970,387 | 7/1976 | Faulhaber et al. | 250/346 |
| 4,156,812 | 5/1979 | Staab | 250/345 |
| 4,180,732 | 12/1979 | Fabinski et al. | 250/345 |

*Primary Examiner*—Davis L. Willis
*Attorney, Agent, or Firm*—Smyth, Pavitt, Siegemund & Martella

[57] ABSTRACT

The cross-sensitivity of a two-beam infrared gas analyzer is reduced by using two differently long cells for the sample gas in the two beam paths. The path with the short sample gas cell is intercepted by a detector cell having highly absorbing wall while the detector cell in the other path is highly reflective, e.g., made of gold. The two detector cells are interconnected by a differential pressure chamber with capacitive pickup.

5 Claims, 1 Drawing Figure

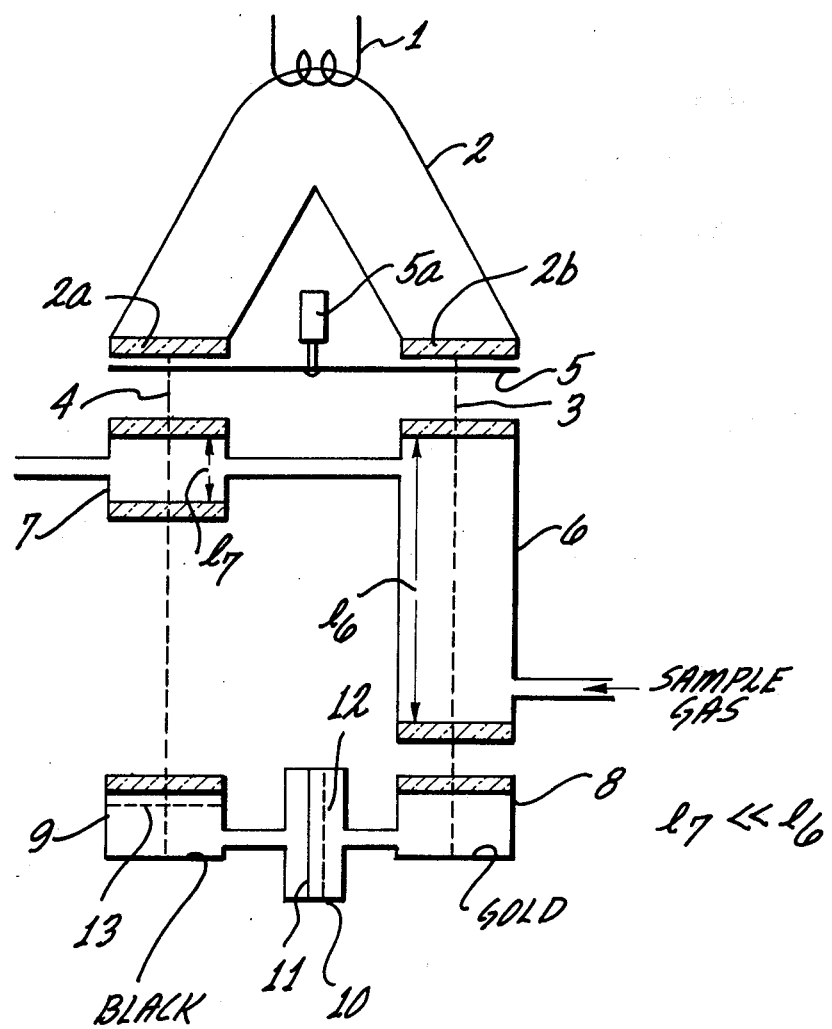

NONDISPERSIVE INFRARED GAS ANALYZER

BACKGROUND OF THE INVENTION

The present invention relates to nondispersive, infrared gas analyzers.

Gas analyzers of the type to which the invention pertains are, for example, constructed as two-beam or two-beam-path instruments, in which a reference beam and a measuring beam of infrared radiation is derived from a common source. A chopper interrupts the two beams periodically to modulate them in an alternating, 180-degree out of phase fashion. One or both of the two beams are attenuated by the sample or measuring gas. In some instances, a reference gas is used in one of the beam paths. In either case, the attenuated beams are detected by radiation detectors which, for example, include cells containing the same type of gas whose concentration is to be detected in the measuring or sample gas. The two detection cells are connected to opposite sides of a differential pressure measuring chamber, being partitioned by a flexible membrane which serves as one electrode of a capacitor. The capacitor is an electrical pickup from which an electrical signal can be derived, being indicative of the concentration of the component of interest in the measuring gas. See, for example, U.S. Pat. Nos. 4,156,812, 3,970,387, 3,937,962, and 3,925,667. Gas analysis on the basis of measuring in some fashion the effect of absorption of radiation by the component of interest depends on frequency selectively by that component. If the sample and measuring gas includes another component whose absorption bands overlap, to at least some extent, the absorption band of the component to be detected, the measuring result will not be accurate and will, in fact, be the more erroneous, the larger the relative content of that other, interfering, component in the measuring gas. This phenomenon is called cross-sensitivity of the analyzer. Reducing cross-sensitivity means, reducing the effect these interfering components have on the measuring result. In other words, a reduction in cross-sensitivity increases the selectivity of the analyzer and its sensitivity with regard to the component of interest; the effective measuring range is enlarged toward the lower end.

Cross-sensitivity has been reduced on the basis of two approaches, also called positive and negative filtering (see, for example, Chemie-Ingenieur-Technik, Vol. 33, 1961, No. 6, pp. 428, 429). Positive filtering, for example, uses a cell filled with measuring gas and placed in the path of one beam, while a cell filled with a nonabsorbing gas is placed in the path of the other beam. Negative filtering describes a situation, in which the two beam paths include cells of similar length, both cells being flown through by the measuring and sample gas, and the one path includes additionally a filter cell filled with gas of the type to be detected. It was found that negative filtering reduces cross-sensitivity to a greater extent than positive filtering.

DESCRIPTION OF THE INVENTION

It is an object of the present invention to improve the sensitivity and selectivity of infrared gas analyzers by reducing the cross-sensitivity thereof.

It is a specific object of the present invention to improve the sensitivity of two-beam infrared gas analyzers, using chopped beam modulation, detection cell means being filled with gas of the type to be detected and being interconnected by a differential pressure-measuring chamber with capacitive pickup.

In accordance with the preferred embodiment of the present invention, it is suggested to provide two differently long cells for sample gas in the two beam paths as per the specific object and to construct the detection cell in the path with the shorter sample gas cell to absorb more of the overall radiation than the walls of the other detection cell. Preferably, the walls of the first-mentioned detection cell should be black, the walls of the other detection cell should be reflective, e.g., made of gold. This construction improves significantly the cross sensitivity of the analyzer, without the use of filters.

DESCRIPTION OF THE DRAWING

While the specification concludes with claims, particularly pointing out and distinctly claiming the subject matter which is regarded as the invention, it is believed that the invention, the objects and features of the invention, and further objects, features and advantages thereof, will be better understood from the following description taken in connection with the accompanying drawings, in which:

The FIGURE shows a schematic view of an example of the preferred embodiment of the present invention for practicing the best mode thereof.

The FIGURE shows a source 1 of infrared radiation, emitting such radiation into two ducts 2, having exit windows 2a and 2b. Accordingly, two beams of radiation are provided along and in two paths, one of which (path 3) could be termed the measuring beam path, while the second one (path 4) would be termed a reference path.

The two beams are alternatingly interrupted by a diaphragm disk 5 which is driven by a motor 5a. Beam path 3 includes a relatively long cell or chamber 6, having suitable entrance and exit windows and being connected, e.g., to receive sample or measuring gas. Beam path 4 includes a relatively short cell or chamber 7, also having a suitable entrance and exit windows and being connected to cell or chamber 6 as well as to a discharge outlet for the sample gas.

It can, thus, be seen that measuring and sample gas flows into cell 6, near the optical exit window; the gas flows through the cell and into cell 7 from which it is discharged. The sequence of flow-through is arbitrary in principle, the flow direction could be reversed.

The short cell 7 has a length $l_7$ and the long cell 6 has a length $l_6$. Decisive is that the one cell, namely cell 6, is much longer than the other one, namely cell 7. Much longer, is to mean that the lengths differ by about one order of magnitude. The length ratio should be at least approximately 1:5 in order to obtain a noticeable effect, but may even be as high as $1:10_3$.

The analyzer includes two detection cells or chambers, 8 and 9, which contain gas of the type to be detected as to its concentration in the measuring and sample gas. The two chambers 8 and 9 communicate with a differential chamber 10 in that chamber 8 is connected to one side of a partitioning diaphragm 11 in chamber 10, and chamber 9 is connected to the other side of the diaphragm. Diaphragm 11 is a flexible electrode and cooperates with another electrode 12, being perforated so that equal pressure exists always on both sides of electrode 12. Any pressure differential between chambers 8 and 9 is, thus, fully effective on diaphragm 11, flexing it accordingly.

The electrodes 11 and 12 are connected to suitable electrical circuitry for generating a signal that relates directly to the pressure differential. These aspects are known per se and do not require elaboration. The capacitor modulation produced in this manner results in a signal that is indicative of the concentration of the gas to be detected in the carrier or sample gas flowing through chambers 6 and 7.

The two cells and chambers 8 and 9 differ in respect to the following features. The interior wall surface of chamber 8 is made of gold, or is gold plated, while the surfaces of chamber 9 are anodized black. Broadly speaking, the walls of cell 8 should be highly reflective in the infrared range, and gold is very suitable for that purpose. The walls of cell 9 should absorb as much infrared radiation as possible; they should be optically black in that range.

A fine wire mesh 13 is disposed in chamber 9, extending all across its effective optical cross section. The wire mesh is also blackened and has a very low heat capacity. The wire mesh serves as a black body which also absorbs practically all of the radiation it intercepts. Due to beam chopping, the incident radiation varies in intensity resulting in corresponding temperature variations of the wire mesh because the latter transfers absorbed heat immediately to the gas in its environment. It should be noted that the absorbing cell 9 is disposed in the path of the short sample gas cell 7. The radiation reaching cell 9 is, thus, comparatively little attenuated in the frequency band of the component gas to be detected.

On the other hand, radiation not directly absorbed by the gas in chamber 8 is almost completely reflected by the golden walls, whereby the various portions of the wall bounce the radiation back and forth. This, in effect, increases the effective length of the radiation path in chamber 8 so that the gas therein will absorb a higher portion of the radiation (of the particular wave lengths and bands) than is absorbed by the gas in chamber 9.

It was found that this combination of features increases the selectivity of response to the gas component to be detected without requiring additional filters. Measuring sensitivity is particularly high because absence of additional filters avoids preabsorption of radiation prior to reaching the detection chambers. Chamber 6 absorbs, of course, much more radiation in the band of interest than chamber 7; the residual radiation of path 4 is almost completely absorbed by the walls of chamber 9 while residual radiation of the selective bands is to be absorbed by the content of chamber 8. It was found, further, that the device is not very temperature sensitive.

The invention is not limited to the embodiments described above; but all changes and modifications thereof, not constituting departures from the spirit and scope of the invention, are intended to be included.

We claim:

1. A nondispersive infrared gas analyzer having a source for infrared radiation as well as means for defining a first and a second path as well as chopper means for periodically interrupting radiation in each of said paths, further including first and second detection cells filled with gas of the type to be detected in the sample gas, the cells being respectively disposed in said first and second paths, there being additionally differential pressure sensing means with capacitive pickup connected to the first and second detection cells for responding to pressure differences in those detection cells and providing an electrical signal representative thereof, the improvement comprising:

a first and a second cell for sample gas, respectively disposed in the first and the second path, the first cell being significantly shorter in the direction of the first path than the second cell; and the walls of the first detection cell absorbing more radiation than the walls of the second detection cells.

2. An analyzer as in claim 1, the walls of the first detection cell being black, the walls of the second detection cell being reflective.

3. An analyzer as in claim 1 or 2, the walls of the second detection cell being made of gold.

4. An analyzer as in claim 1 or 2, the first cell including additional absorbing means having a low heat capacity.

5. An analyzer as in claim 4, the additional means being a blackened wire mesh.

* * * * *